(12) United States Patent
Shameli et al.

(10) Patent No.: US 12,303,215 B2
(45) Date of Patent: *May 20, 2025

(54) CURETTE WITH NAVIGATION SENSOR

(71) Applicant: Acclarent, Inc., Irvine, CA (US)

(72) Inventors: Ehsan Shameli, Irvine, CA (US);
Itzhak Fang, Irvine, CA (US); Babak Ebrahimi, Irvine, CA (US)

(73) Assignee: Acclarent, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/513,814

(22) Filed: Nov. 20, 2023

(65) Prior Publication Data

US 2024/0081919 A1 Mar. 14, 2024

Related U.S. Application Data

(63) Continuation of application No. 16/299,733, filed on Mar. 12, 2019, now Pat. No. 11,832,890.

(Continued)

(51) Int. Cl.
*A61B 17/3207* (2006.01)
*A61B 34/20* (2016.01)
*A61B 17/00* (2006.01)

(52) U.S. Cl.
CPC ...... *A61B 34/20* (2016.02); *A61B 17/320708* (2013.01); *A61B 2017/0042* (2013.01); *A61B 2017/00477* (2013.01); *A61B 2017/00743* (2013.01); *A61B 2034/2051* (2016.02); *A61B 2217/005* (2013.01); *A61B 2217/007* (2013.01)

(58) Field of Classification Search
CPC .................. A61B 34/20; A61B 17/320708
See application file for complete search history.

(56) References Cited

U.S. PATENT DOCUMENTS 1,080,928 A * 12/1913 Romeo .................... A41B 1/16
2/127
4,043,322 A * 8/1977 Robinson ............... A61B 1/303
606/160

(Continued)

FOREIGN PATENT DOCUMENTS

GB          2423369 A     8/2006
JP      2007-044507 A     2/2007

(Continued)

OTHER PUBLICATIONS

International Search Report and Written Opinion dated Oct. 11, 2019, for International Application No. PCT/IB2019/052997, 16 pages.

(Continued)

*Primary Examiner* — Rochelle D Turchen
(74) *Attorney, Agent, or Firm* — Morgan, Lewis & Bockius LLP

(57) ABSTRACT

An apparatus includes a shaft assembly, an end effector, and a sensor. The shaft assembly defines a longitudinal axis. The end effector is positioned at a distal end of the shaft assembly. A portion of the end effector is offset from the longitudinal axis. The sensor is configured to generate a signal in response to a magnetic field. The signal is configured to indicate a position of the end effector within three-dimensional space. The sensor is coaxially positioned about the longitudinal axis.

19 Claims, 6 Drawing Sheets

Related U.S. Application Data

(60) Provisional application No. 62/658,688, filed on Apr. 17, 2018.

(56) References Cited

U.S. PATENT DOCUMENTS

| | | | |
|---|---|---|---|
| 6,277,064 B1 * | 8/2001 | Yoon | A61B 1/051 600/173 |
| 7,720,521 B2 | 5/2010 | Chang et al. | |
| 8,320,711 B2 | 11/2012 | Altmann et al. | |
| 8,702,626 B1 | 4/2014 | Kim et al. | |
| 10,405,875 B2 * | 9/2019 | Voic | A61B 17/320068 |
| 2007/0078484 A1 | 4/2007 | Talarico et al. | |
| 2009/0023987 A1 | 1/2009 | Okada et al. | |
| 2010/0076303 A1 | 3/2010 | McKinley | |
| 2011/0060214 A1 | 3/2011 | Makower | |
| 2014/0364725 A1 | 12/2014 | Makower | |
| 2016/0008083 A1 | 1/2016 | Kesten et al. | |
| 2016/0310042 A1 | 10/2016 | Kesten et al. | |
| 2018/0310886 A1 | 11/2018 | Salazar et al. | |
| 2019/0015166 A1 | 1/2019 | Mahoney et al. | |
| 2019/0314089 A1 | 10/2019 | Shameli et al. | |

FOREIGN PATENT DOCUMENTS

| | | |
|---|---|---|
| JP | 2016-501632 A | 1/2016 |
| JP | 2018-043009 A | 3/2018 |
| WO | WO 2017/052704 A2 | 3/2017 |

OTHER PUBLICATIONS

Japanese Notification of Reasons for Refusal dated Feb. 14, 2023, for Application No. 2020-557332, 5 pages.

* cited by examiner

CURETTE WITH NAVIGATION SENSOR

PRIORITY

This application is a continuation of U.S. patent application Ser. No. 16/299,733, entitled "Curette With Navigation Sensor," filed Mar. 12, 2019, which claims priority to U.S. Provisional Patent App. No. 62/658,688, entitled "Curette With Navigation Sensor," filed Apr. 17, 2018, the disclosure of which is incorporated by reference herein.

BACKGROUND

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit alternating current electromagnetic fields and/or are responsive to externally generated alternating current electromagnetic fields) mounted thereon are used to perform the procedure while the sensors send data to the computer indicating the current position of each surgical instrument. The computer correlates the data it receives from the instrument-mounted sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. In this manner, the surgeon is able to know the precise position of each sensor-equipped instrument by viewing the video monitor even if the surgeon is unable to directly visualize the instrument itself at its current location within the body.

An example of an electromagnetic IGS systems that may be used in ENT and sinus surgery is the CARTO® 3 System by Biosense-Webster, Inc., of Irvine, California. When applied to functional endoscopic sinus surgery (FESS), balloon sinuplasty, and/or other ENT procedures, the use of IGS systems allows the surgeon to achieve more precise movement and positioning of the surgical instruments than can be achieved by viewing through an endoscope alone. As a result, IGS systems may be particularly useful during performance of FESS, balloon sinuplasty, and/or other ENT procedures where anatomical landmarks are not present or are difficult to visualize endoscopically.

Navigation of the three-dimensional views of the areas surrounding the operative field (e.g., rotating or moving a viewpoint within three-dimensional space) may be accomplished via interaction with an interface device, such as a keyboard or mouse, of an IGS system. These types of interface devices might not be intended for use in a sterile environment, and therefore may not located within reach of a clinician that is performing a medical procedure with the assistance of an IGS system. As a result, clinicians may need to relay navigation instructions to an assistant in another room or area, who will then use the interface device to provide the three-dimensional views that the clinician desires. This process can be time consuming and error prone.

While several systems and methods have been made and used in ENT procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
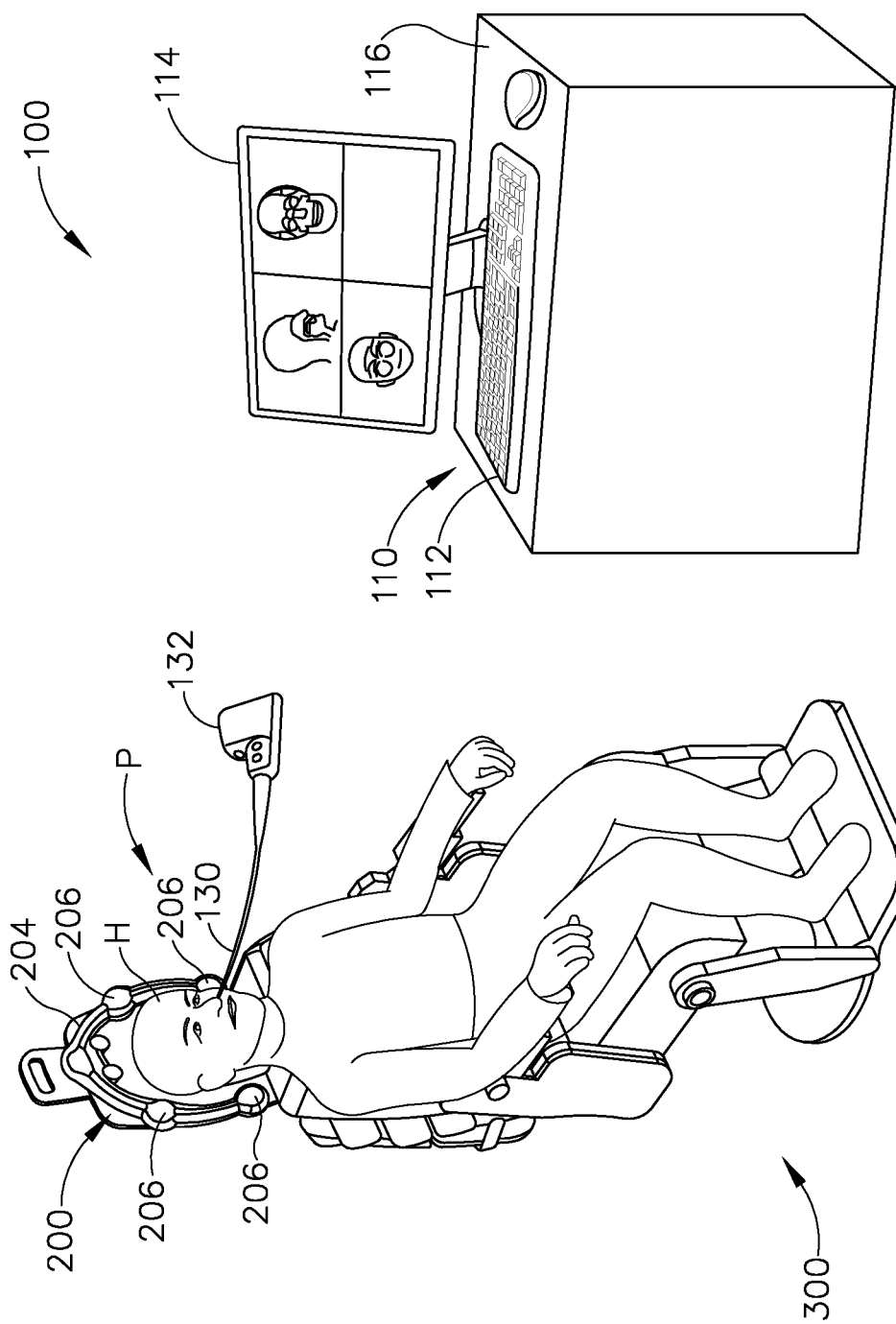
FIG. 1 depicts a schematic view of an exemplary sinus surgery navigation system being used on a patient seated in an exemplary medical procedure chair.
Figure 2:
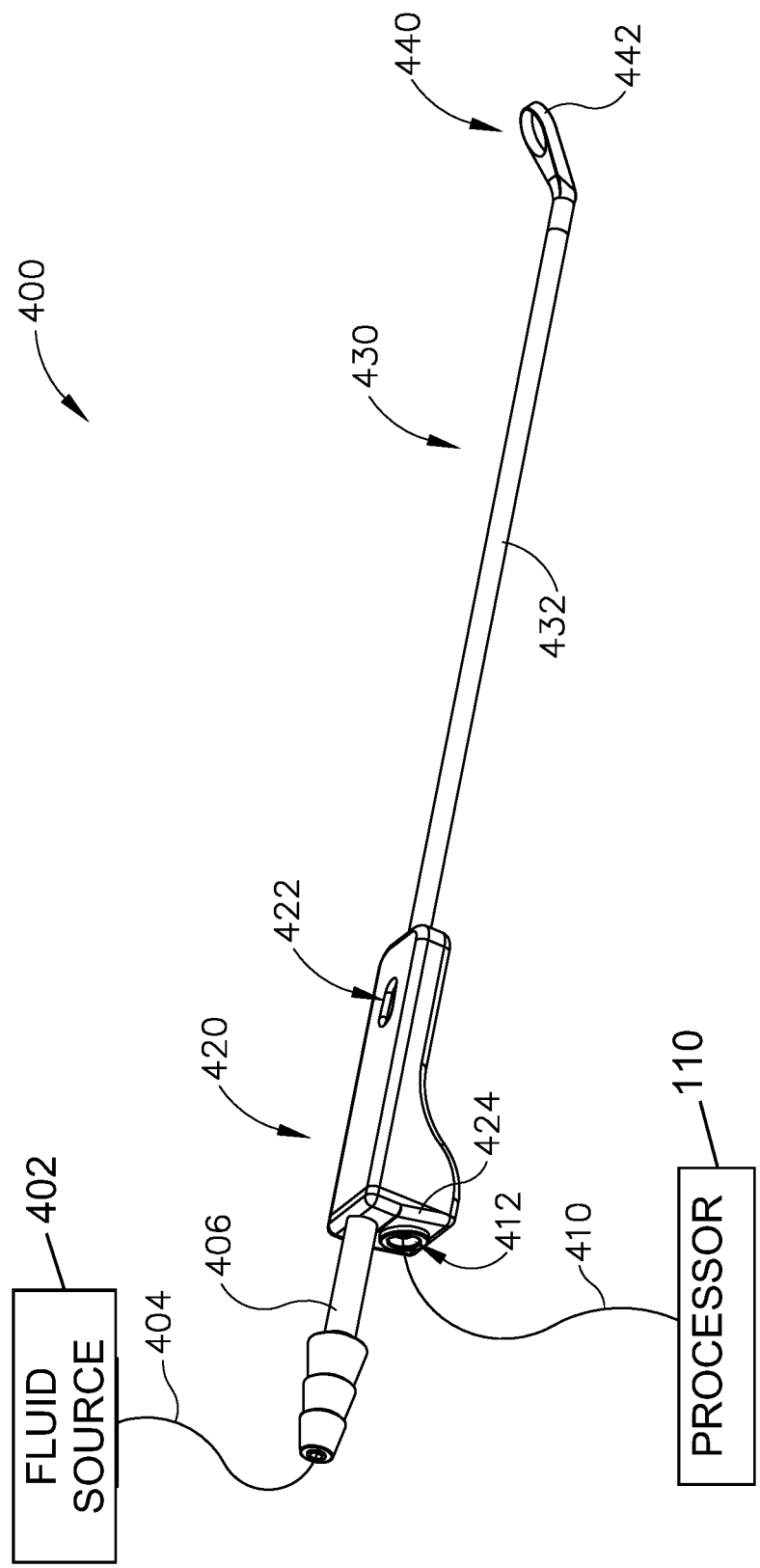
FIG. 2 depicts a perspective view of an exemplary curette instrument configured for use with the system of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. EXEMPLARY IMAGE GUIDED SURGERY NAVIGATION SYSTEM

FIG. 1 shows an exemplary IGS navigation system (100) enabling an ENT procedure to be performed using image guidance. In some instances, IGS navigation system (100) is used during a procedure where a dilation instrument assembly (not shown) is used to dilate the ostium of a paranasal sinus; or to dilate some other anatomical passageway (e.g., within the ear, nose, or throat, etc.). As another merely illustrative example, IGS navigation system (100) may be used during performance of any other kind of medical procedure within a patient's head, including but not limited to within the patient's nasal cavity, paranasal sinuses, Eustachian tubes, etc.; elsewhere within a patient's head; within a patient's throat; or elsewhere within a patient's body. Various suitable locations and clinical contexts in which IGS navigation system (100) may be used will be apparent to those of ordinary skill in the art in view of the teachings herein.

In addition to or in lieu of having the components and operability described herein IGS navigation system (100) may be constructed and operable in accordance with at least some of the teachings of U.S. Pat. No. 8,702,626, entitled "Guidewires for Performing Image Guided Procedures," issued Apr. 22, 2014, the disclosure of which is incorporated by reference herein; U.S. Pat. No. 8,320,711, entitled "Anatomical Modeling from a 3-D Image and a Surface Mapping," issued Nov. 27, 2012, the disclosure of which is incorporated by reference herein; U.S. Pat. No. 7,720,521, entitled "Methods and Devices for Performing Procedures within the Ear, Nose, Throat and Paranasal Sinuses," issued May 18, 2010, the disclosure of which is incorporated by reference herein; U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein; U.S. Pat. Pub. No. 2016/0310042, entitled "System and Method to Map Structures of Nasal Cavity," published Oct. 27, 2016, issued as U.S. Pat. No. 10,362,965 on Jul. 30, 2019; and U.S. Pat. Pub. No. 2011/0060214, entitled "Systems and Methods for Performing Image Guided Procedures within the Ear, Nose, Throat and Paranasal Sinuses," published Mar. 10, 2011, now abandoned, the disclosure of which is incorporated by reference herein.

IGS navigation system (100) of the present example comprises a field generator assembly (200), which comprises set of magnetic field generators (206) that are integrated into a horseshoe-shaped frame (204). Field generators (206) are operable to generate alternating magnetic fields of different frequencies around the head of the patient. Field generators (206) thereby enable tracking of the position of a navigation guidewire (130) that is inserted into the head of the patient. Various suitable components that may be used to form and drive field generators (206) will be apparent to those of ordinary skill in the art in view of the teachings herein.

In the present example, frame (204) is mounted to a chair (300), with the patient (P) being seated in the chair (300) such that frame (204) is located adjacent to the head (H) of the patient (P). By way of example only, chair (300) and/or field generator assembly (200) may be configured and operable in accordance with at least some of the teachings of U.S. Pat. Pub. No. 2018/0310886, entitled "Apparatus to Secure Field Generating Device to Chair," published Nov. 1, 2018, issued as U.S. Pat. No. 10,561,370 on Feb. 18, 2020, the disclosure of which is incorporated by reference herein.

IGS navigation system (100) of the present example further comprises a processor (110), which controls field generators (206) and other elements of IGS navigation system (100). For instance, processor (110) is operable to drive field generators (206) to generate alternating current electromagnetic fields; and process signals from navigation guidewire (130) to determine the location of a sensor (not shown) in navigation guidewire (130) within the head (H) of the patient (P). Processor (110) comprises a processing unit communicating with one or more memories. Processor (110) of the present example is mounted in a console (116), which comprises operating controls (112) that include a keypad and/or a pointing device such as a mouse or trackball. A physician uses operating controls (112) to interact with processor (110) while performing the surgical procedure.

A coupling unit (132) is secured to the proximal end of a navigation guidewire (130). Coupling unit (132) of this example is configured to provide wireless communication of data and other signals between console (116) and navigation guidewire (130). While coupling unit (132) of the present example couples with console (116) wirelessly, some other versions may provide wired coupling between coupling unit (132) and console (116). Various other suitable features and functionality that may be incorporated into coupling unit (132) will be apparent to those of ordinary skill in the art in view of the teachings herein.

Navigation guidewire (130) of the present example includes a sensor (not shown) that is responsive within the fields generated by field generators (206). In the present example, the sensor of navigation guidewire (130) comprises at least one coil at the distal end of navigation guidewire (130). When such a coil is positioned within an alternating current electromagnetic field generated by field generators (206), such positioning may generate electrical current in the coil, and this electrical current may be communicated along the electrical conduit(s) in navigation guidewire (130) and further to processor (110) via coupling unit (132). This phenomenon may enable IGS navigation system (100) to determine the location of the distal end of navigation guidewire (130) within a three-dimensional space (i.e., within the head (H) of the patient (P)). To accomplish this, processor (110) executes an algorithm to calculate location coordinates of the distal end of navigation guidewire (130) from the position related signals of the coil(s) in navigation guidewire (130).

Processor (110) uses software stored in a memory of processor (110) to calibrate and operate system (100). Such operation includes driving field generators (206), processing data from navigation guidewire (130), processing data from operating controls (112), and driving display screen (114). Processor (110) is further operable to provide video in real time via display screen (114), showing the position of the distal end of navigation guidewire (130) in relation to a video camera image of the patient's head (H), a CT scan image of the patient's head (H), and/or a computer generated three-dimensional model of the anatomy within and adjacent to the patient's nasal cavity. Display screen (114) may display such images simultaneously and/or superimposed on each other during the surgical procedure. Such displayed images may also include graphical representations of instruments that are inserted in the patient's head (H), such as navigation guidewire (130), such that the operator may view the virtual rendering of the instrument at its actual location in real time. By way of example only, display screen (114) may provide images in accordance with at least some of the teachings of U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein. In the event that the operator is also using an endoscope, the endoscopic image may also be provided on display screen (114).

Those of ordinary skill in the art will recognize that, when navigation guidewire (130) is coupled with a medical instrument, the images provided through display screen (114) may help guide the operator in maneuvering and otherwise manipulating the medical instrument within the patient's head (H) and/or elsewhere within the anatomy of the patient (P).

II. EXEMPLARY CURETTE WITH NAVIGATION SENSOR

Navigation guidewire (130) may be particularly useful with medical instruments (e.g., catheters, etc.) that include a lumen that is capable of accommodating navigation guidewire (130). If navigation guidewire (130) is disposed in such a lumen, and the distance between a sensor in navigation guidewire (130) and a structural feature of the medical instrument is known (e.g., substantially coincident), then IGS system (100) may essentially "know" where that structural feature of the medical instrument is located within the patient (P), based on the sensed location of the sensor in navigation guidewire (130). However, using a navigation guidewire (130) in combination with another instrument may complicate the handling of the instrument or other aspects of a medical procedure, requiring the manipulation of two or more devices (e.g., the guidewire and the instrument) simultaneously. It may therefore be desirable to provide a modified version of the otherwise conventional instrument by incorporating a navigation sensor into the instrument. This may enable the instrument to have the navigational functionality of navigation guidewire (130) without requiring manipulation of a separate device such as navigation guidewire (130).

FIGS. 2-8 show an exemplary curette instrument (400) that includes a navigation sensor (450) that is like the sensor of navigation guidewire (130). Curette instrument (400) of this example includes a grip (420), a shaft assembly (430), and an end effector (440). Grip (420) is sized and configured to be grasped by a single hand of an operator. Shaft assembly (430) extends distally from grip (420). End effector (440) is positioned at the distal end of shaft assembly (430). An end cap (424) is located at the proximal end of grip (420). A fluid fitting (406) extends proximally from end cap (424). Fluid fitting (406) is in fluid communication with a fluid conduit (404) and with shaft assembly (430). Fluid fitting (406) is barbed in the present example, though it should be understood that fluid fitting (406) may have any other suitable configuration (e.g., luer feature, etc.). Fluid conduit (404) couples fluid fitting (406) with a fluid source (402). By way of example only, fluid conduit (404) may comprise a flexible tube. By way of further example only, fluid source (402) may comprise a source of saline, a source of suction, a source of medicinal fluid, and/or a source of any other suitable kind of fluid(s).

Figure 4:
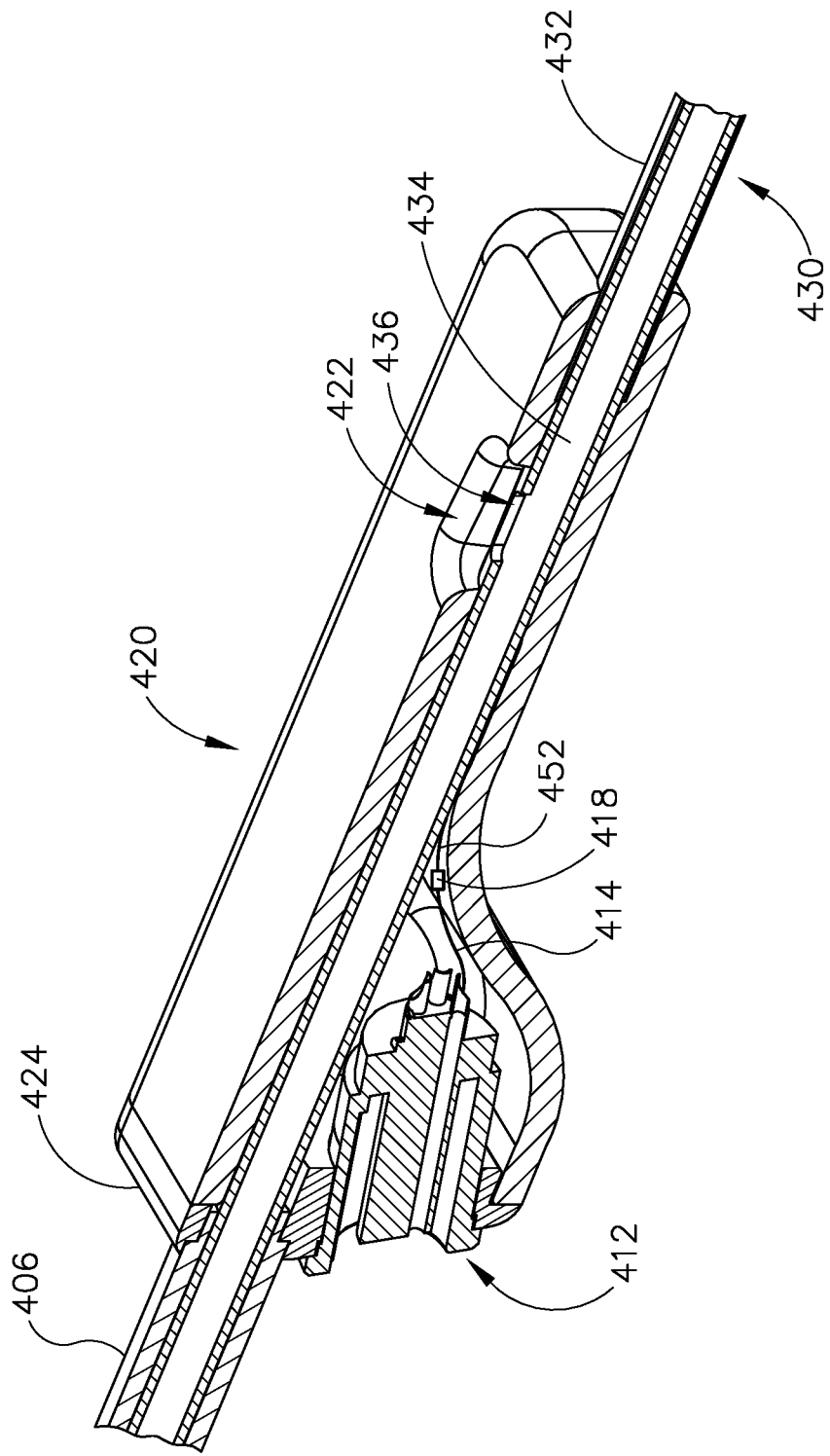
FIG. 4 depicts a side perspective cross-sectional view of a grip portion of the curette instrument of FIG. 2.

A connector (412) is also located at end cap (424). In the present example, connector (412) is removably coupled with processor (110) of IGS navigation system (100) via a wire (410). In some other versions, connector (412) is coupled with processor (110) wirelessly. Various suitable ways in which curette instrument (400) may communicate wirelessly with processor (110) will be apparent to those of ordinary skill in the art in view of the teachings herein. As shown in FIG. 4, connector (412) is also coupled with a storage device (418) via a wire (414); and with a sensor (450) via another wire (452). Those of ordinary skill in the art will appreciate that connector (412) may be coupled with storage device (418) and sensor (450) in various different ways. Storage device (418) is fully contained in grip (420) in the present example. Also in the present example, storage device (418) comprises an EEPROM. The EEPROM stores the calibration information for sensor (450), thereby enabling processor (110) to calibrate to instrument (110) without requiring the operator to manually calibrate. Other suitable forms that storage device (418) may take, as well as other kinds of information that may be stored by storage device (418), will be apparent to those of ordinary skill in the art in view of the teachings herein.

Figure 3:
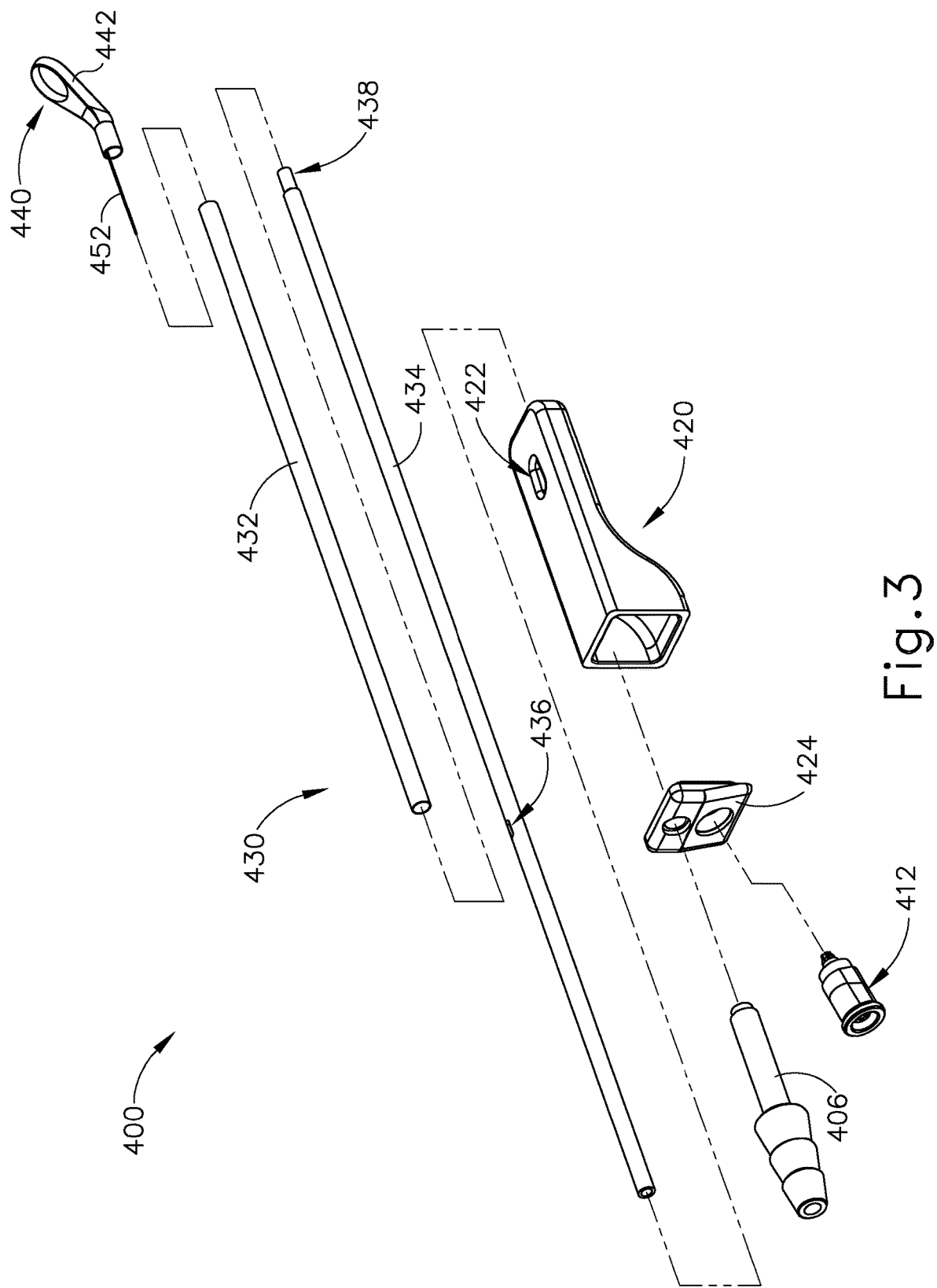
FIG. 3 depicts an exploded perspective view of the curette instrument of FIG. 2.

As best seen in FIG. 3, shaft assembly (430) of the present example comprises an inner cannula (434) and an outer sheath (432). Outer sheath (432) is coaxially disposed about inner cannula (434). Inner cannula (434) defines an inner lumen that is in fluid communication with fluid fitting (406). Inner cannula (434) includes a lateral opening (436) that is also in fluid communication with the lumen of inner cannula (434). The distal end of inner cannula (434) includes a neck-down region (438). Neck-down region (438) has an outer diameter that is smaller than the outer diameter of the rest of inner cannula (434) (i.e., the region of inner cannula (434) that is proximal to neck-down region (438)). Shaft assembly (430) is fully rigid in the present example. In some other versions, at least a portion of shaft assembly (430) is malleable or otherwise flexible.

As best seen in FIG. 4, grip (420) includes a lateral opening (422) that aligns with lateral opening (436) of inner cannula (434). Openings (422, 436) cooperate to provide a path for atmospheric air to reach the lumen of inner cannula (434). Lateral opening (422) is positioned to be selectively covered or uncovered by a finger (e.g., thumb) of the hand of the operator that is grasping grip (420), to thereby prevent or permit atmospheric air to enter the lumen of inner cannula (434) via openings (422, 436). For instance, in versions where fluid source (402) comprises a source of suction, and when the operator wishes to apply suction to a site within a patient via shaft assembly (430), the operator may cover openings (422, 436) to thereby effectively seal openings (422, 436). When the operator wishes to cease communication of suction to the site within the patient via shaft assembly (430), without deactivating fluid source (402), the operator may simply uncover openings (422, 436). This will allow the suction to be communicated to atmosphere via openings (422, 436), such that the suction does not reach the site in the patient at the distal end of shaft assembly (430). While curette instrument (400) of the present example provides suction capabilities, some variations of curette instrument (400) may lack suction capabilities. For instance, fluid source (402), fluid fitting (406), and lateral opening (422) may be omitted. In versions lacking suction capabilities, inner cannula (434) may still have a lumen (e.g., to enable insertion of other instruments through cannula (434)). Alternatively, inner cannula (434) may lack a lumen.

Figure 5:
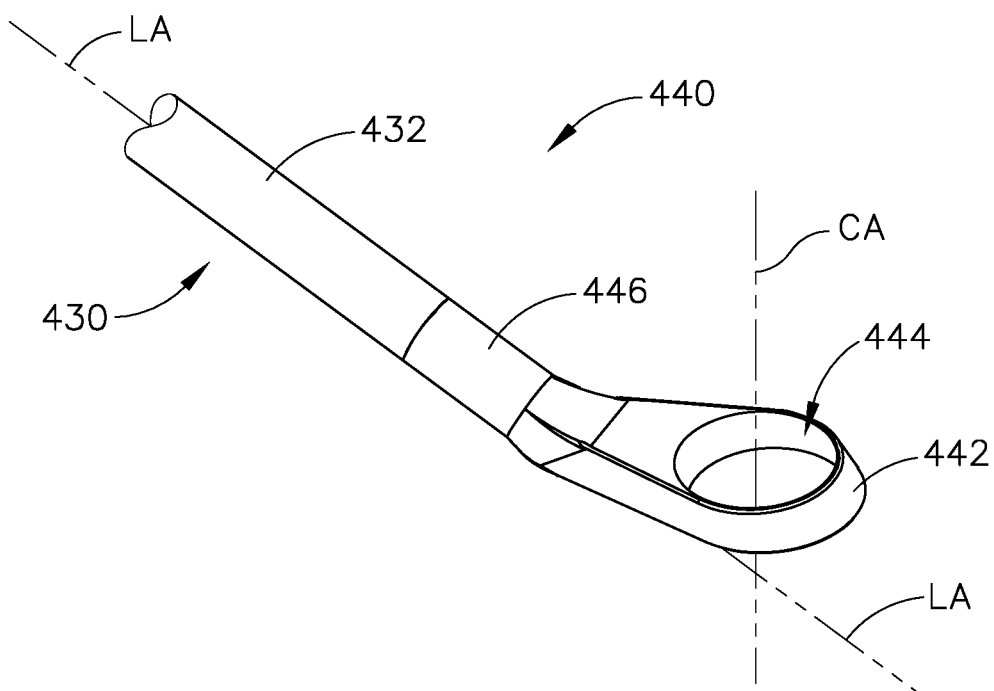
FIG. 5 depicts a perspective view of a distal end portion of the curette instrument of FIG. 2.
Figure 6:
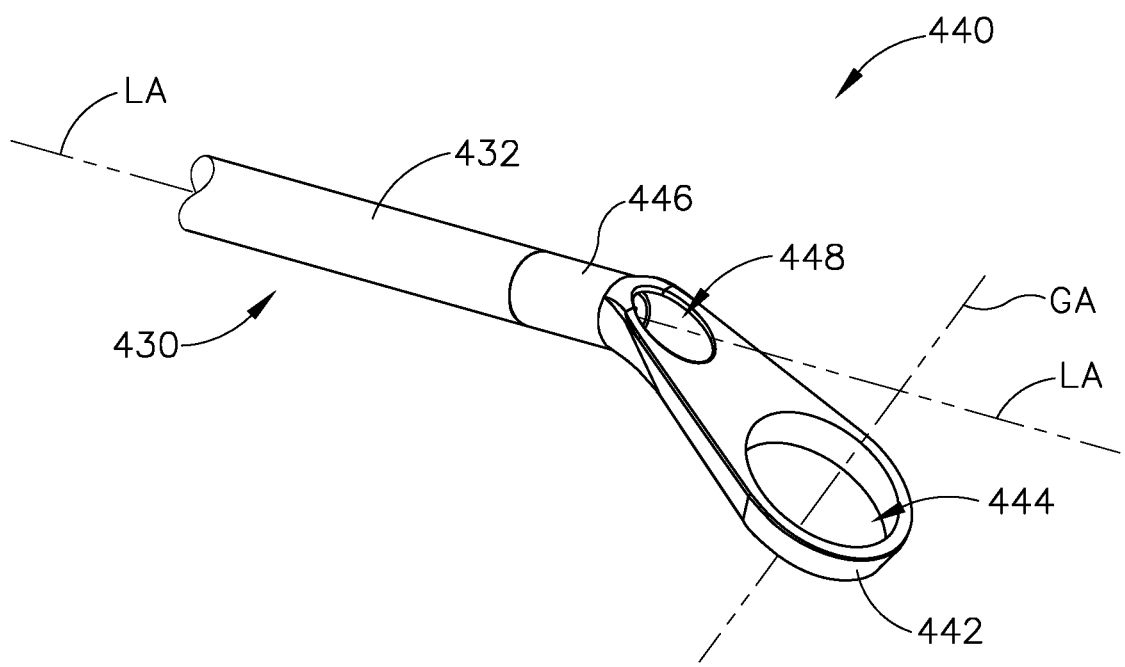
FIG. 6 depicts another perspective view of the distal end portion of the curette instrument of FIG. 2.

As shown in FIGS. 5-8, end effector (440) of the present example, end effector (440) comprises a loop blade (442) that defines an opening (444). A central axis (CA) passes perpendicularly through the center of opening (444). In the present example, as shown in FIGS. 5-6, central axis (CA) is obliquely oriented relative to the central longitudinal axis (LA) of shaft assembly (430). In some other versions, central axis (CA) is perpendicular to longitudinal axis (LA). Loop blade (442) extends along a plane that is also obliquely oriented relative to the central longitudinal axis (LA) of shaft assembly (430) in this example. Moreover, loop blade (442) extends generally transversely relative to the central longitudinal axis (LA) and is not symmetric about the central longitudinal axis (LA) in this example.

A sleeve portion (446) extends proximally relative to loop blade (442). Sleeve portion (446) fits over sensor (450) and cuff (460), which are coaxially positioned about neck-down region (438) of inner cannula (434). The proximal end of sleeve portion (446) abuts the distal end of outer sheath (432). Sleeve portion (446) and outer sheath (432) have the same outer diameter in this example, thereby providing a smooth transition from shaft assembly (430) to end effector (440).

As best seen in FIG. 6, end effector (440) defines an opening (448) that is coaxially aligned with the longitudinal axis (LA) of shaft assembly (430). Opening (448) is in fluid communication with the lumen of inner cannula (434). Thus, fluid communicated from fluid source (402) to inner cannula (434) via fluid conduit (404) and fluid fitting (406) will be further communicated to opening (448). Opening (448) may thus be used to communicate saline or some other liquid to a target site in a patient, apply suction to a target site in a patient, or be otherwise used. As noted above, in some other variations, fluid source (402) is omitted. In some such versions, another instrument is selectively inserted into the lumen of inner cannula (434) and reaches the target site in the patient via the lumen of inner cannula (434) and opening (448). By way of example only, a laser instrument, injection needle, dilation catheter, and/or other kind of instrument may be passed through inner cannula (434) and opening (448) to reach the target site in the patient. In some other versions, opening (448) is omitted.

As another merely illustrative example, inner cannula (434) may lack a lumen. In other words, inner cannula (434) may be replaced with a solid rod in some variations. As yet another merely illustrative example, the lumen of inner cannula (434) may extend along only a portion of the length of inner cannula (434). Similarly, the lumen of inner cannula (434) may terminate proximal to end effector (440), such that opening (448) is omitted.

Sensor (450) of the present example comprises a wire coil that induces an electrical signal within the alternating magnetic fields generated by field generators (206). This signal generated by sensor (450) is indicative of the position and orientation of sensor (450) within the alternating magnetic fields generated by field generators (206). The distance and positioning between sensor (450) and loop blade (442) are constant in the present example, such that processor (110) may determine the position of loop blade (442) within the patient based on the sensed location of sensor (450) in the patient. Thus, an operator may view display screen (114) to observe the real-time positioning of loop blade (442) superimposed over a CT image and/or other image representing anatomical structures within the patient. While only a single wire coil is used to form sensor (450) in the present example, sensor (450) may alternatively comprise two or more coils. When a single coil is used, the coil may be wrapped about a single axis. When two or more coils are used, the coils may be wrapped about different respective axes. In some variations, sensor (450) comprises three coils wrapped about three different axes. In some such variations, the three axes are perpendicular to each other.

Figure 7:
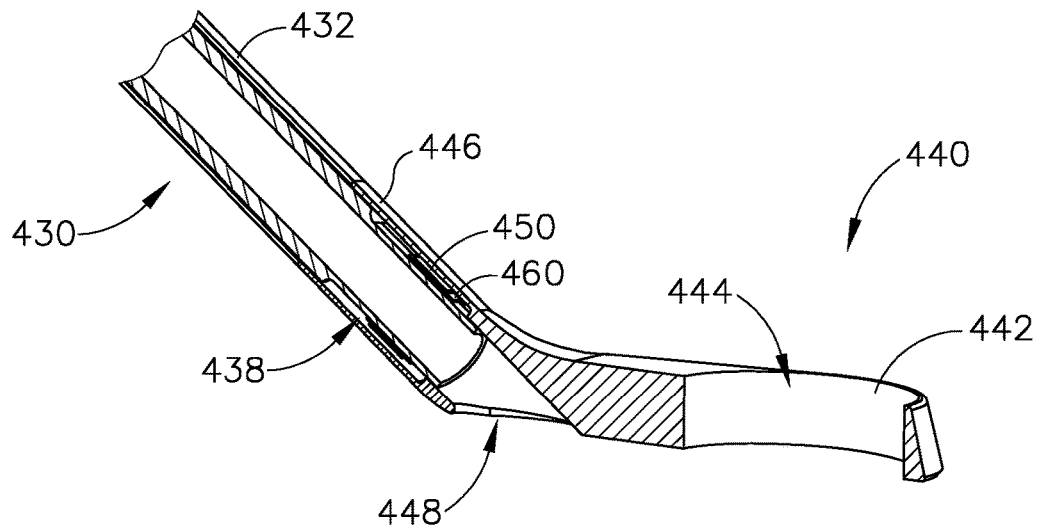
FIG. 7 depicts a side perspective cross-sectional view of the distal end portion of the curette instrument of FIG. 2.

As best seen in FIG. 7, cuff (460) is concentrically disposed between sensor (450) and neck-down region (438) of inner cannula (434). Cuff (460) is formed of an electrically insulating material (e.g., polyimide, etc.) and is slightly longer than sensor (450), such that cuff (460) electrically isolates sensor (450) from neck-down region (438) of inner cannula (434).

Figure 8:
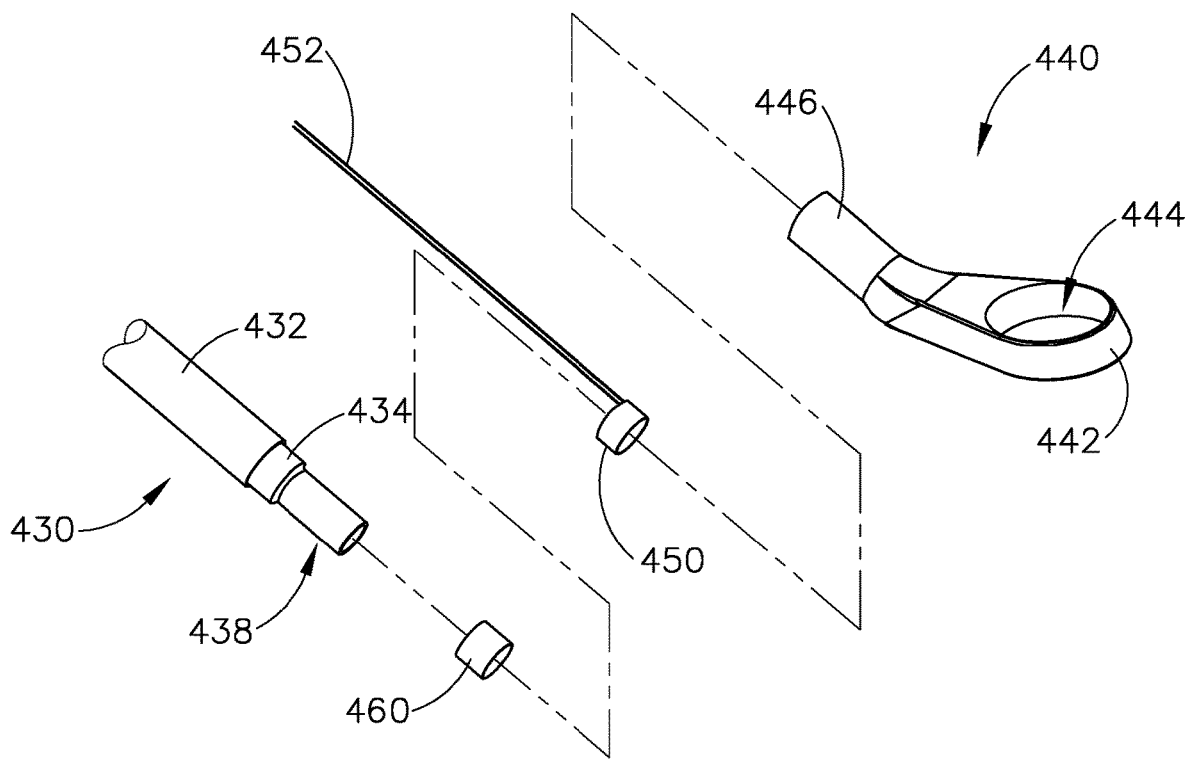
FIG. 8 depicts an exploded perspective view of the distal end portion of the curette instrument of FIG. 2.

While only a portion of wire (452) is shown in FIGS. 3-4 and 8, wire (452) extends along the full length of shaft assembly (430) to couple sensor (450) with storage device (418). In the present example, wire (452) is captured between outer sheath (432) and inner cannula (434). Alternatively, sensor (450) may be coupled with storage device (418) in any other suitable fashion as will be apparent to those of ordinary skill in the art in view of the teachings herein. While storage device (418) is interposed between sensor (450) and connector (412) in the present example, sensor (450) may instead be coupled directly with connector (412) in other versions. In such versions, storage device (418) may be coupled with connector (412) in parallel. As another variation, storage device (418) may simply be omitted.

While sensor (450) is incorporated into a curette instrument (400) in this example, sensor (450) may instead be incorporated into various other kinds of instruments, including but not limited to picks, rosette, pointer, elevator, rosens, endoscopes, and/or various other kinds of instruments. Other kinds of instruments that may incorporate a sensor (450) will be apparent to those of ordinary skill in the art in view of the teachings herein. In some variations, end effector (440) is removably coupled with shaft assembly (430), such that end effector (440) may be replaced with various other kinds of end effectors having various other kinds of configurations. By way of example only, such modular end effectors may all have structures similar to sleeve portion (446). Such sleeve portions (446) may selectively couple with the distal end of shaft assembly (430) via threading, via bayonet mounting, via press-fitting, via snap-fitting, and/or in any other suitable fashion as will be apparent to those of ordinary skill in the art in view of the teachings herein.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a shaft assembly, wherein the shaft assembly defines a longitudinal axis; (b) an end effector positioned at a distal end of the shaft assembly, wherein a portion of the end effector is offset from the longitudinal axis; and (c) a sensor, wherein the sensor is configured to generate a signal in response to a magnetic field, wherein the signal is configured to indicate a position of the end effector within three-dimensional space, wherein the sensor is coaxially positioned about the longitudinal axis.

Example 2

The apparatus of Example 1, wherein the shaft assembly is straight.

Example 3

The apparatus of any one or more of Examples 1 through 2, wherein the shaft assembly is rigid.

Example 4

The apparatus of any one or more of Examples 1 through 3, wherein the shaft assembly comprises an inner cannula and an outer sheath, wherein the outer sheath is coaxially disposed about the inner cannula.

Example 5

The apparatus of any one or more of Examples 1 through 4, wherein the shaft assembly defines a lumen.

Example 6

The apparatus of Example 5, wherein the lumen extends coaxially along the longitudinal axis.

Example 7

The apparatus of any one or more of Examples 5 through 6, further comprising a fluid source coupled with the lumen.

Example 8

The apparatus of Example 7, wherein the fluid source comprises one or both of a source of saline or a source of suction.

Example 9

The apparatus of any one or more of Examples 5 through 8, wherein the end effector defines an opening in communication with the lumen.

Example 10

The apparatus of Example 9, wherein the opening is positioned on the longitudinal axis.

Example 11

The apparatus of any one or more of Examples 1 through 10, wherein the end effector includes a loop blade.

Example 12

The apparatus of Example 11, wherein the loop blade defines an opening positioned on a central axis, wherein the central axis is offset from the longitudinal axis.

Example 13

The apparatus of Example 12, wherein the central axis is oriented obliquely relative to the longitudinal axis.

Example 14

The apparatus of any one or more of Examples 1 through 13, further comprising a grip, wherein the shaft assembly extends distally from the grip.

Example 15

The apparatus of Example 14, wherein the shaft assembly defines a lumen, wherein the grip defines a lateral opening in fluid communication with the lumen.

Example 16

The apparatus of any one or more of Examples 14 through 15, further comprising a storage device.

Example 17

The apparatus of Example 16, wherein the storage device is located in the grip.

Example 18

The apparatus of any one or more of Examples 16 through 17, wherein the storage device comprises an EEPROM.

Example 19

The apparatus of any one or more of Examples 16 through 18, wherein the storage device stores calibration information associated with the sensor.

Example 20

The apparatus of any one or more of Examples 1 through 19, further comprising an insulating cuff captured between the sensor and a distal portion of the shaft assembly.

Example 21

An apparatus, comprising: (a) a grip; (b) a shaft assembly extending distally from the grip, wherein the shaft assembly defines a longitudinal axis; (c) an end effector positioned at a distal end of the shaft assembly, wherein the end effector comprises a loop blade, wherein the loop blade is offset from the longitudinal axis; and (d) a sensor, wherein the sensor is configured to generate a signal in response to a magnetic field, wherein the signal is configured to indicate a position of the loop blade within three-dimensional space, wherein the sensor is coaxially positioned about the longitudinal axis.

Example 22

A method, comprising: (a) inserting a distal end of an instrument into a patient; (b) observing a display showing the position of the distal end of the instrument in the patient in real-time, wherein the display is driven by a processor processing signals from a sensor in the distal end of the instrument, wherein the sensor generates the signals in response to a magnetic field; (c) engaging a transversely extending portion of the distal end of the instrument with tissue in the patient based on the observed position, wherein the transversely extending portion of the distal end is offset from a longitudinal axis of a shaft assembly of the instrument, wherein the sensor is coaxially positioned about the longitudinal axis.

Example 23

The method of Example 22, wherein the transversely extending portion comprises a blade.

Example 24

The method of any one or more of Examples 22 through 23, further comprising communicating a fluid to a target site in the patient via an opening at the distal end of the instrument.

Example 25

The method of Example 24, wherein the act of communicating a fluid comprises communicating one or both of suction or liquid.

IV. MISCELLANEOUS

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
a shaft assembly extending along a longitudinal axis;
a rigid end effector fixed relative to the shaft assembly, the rigid end effector having a central axis that is obliquely oriented relative to the longitudinal axis;
a first opening that defines the central axis and is positioned along the longitudinal axis;
a second opening extending through the rigid end effector and being coplanar with the first opening; and
a sensor disposed at a position along the longitudinal axis of the shaft assembly, the sensor being configured to generate a signal in response to a magnetic field, the signal being configured to indicate a position of the rigid end effector within three-dimensional space.

2. The apparatus of claim 1, wherein the rigid end effector comprises a loop blade that extends transversely relative to the longitudinal axis and is not symmetric about the longitudinal axis.

3. The apparatus of claim 1, wherein the shaft assembly is straight.

4. The apparatus of claim 1, wherein the shaft assembly is rigid.

5. The apparatus of claim 1, wherein a portion of the shaft assembly is malleable or flexible.

6. The apparatus of claim 1, wherein the shaft assembly comprises an inner cannula and an outer sheath that is coaxially disposed about the inner cannula.

7. The apparatus of claim 1, wherein the shaft assembly defines a lumen that extends coaxially along the longitudinal axis.

8. The apparatus of claim 7, further comprising a grip configured to be gripped by a user, the shaft assembly extending distally from the grip, the grip defining a lateral opening in fluid communication with the lumen.

9. The apparatus of claim 8, wherein the lateral opening is positioned to be selectively covered or uncovered by a finger of a hand of an operator that is grasping the grip, to selectively permit atmospheric air to enter the lumen through the opening.

10. The apparatus of claim 7, wherein the opening is in communication with the lumen.

11. The apparatus of claim 8, further comprising a fluid source coupled with the lumen, the fluid source comprising one or both of a source of saline or a source of suction.

12. An apparatus, comprising:
a shaft assembly defining a longitudinal axis, the shaft assembly including a distal end;
a rigid end effector fixed relative to the distal end of the shaft assembly, the rigid end effector including first and second openings, the first opening being positioned along the longitudinal axis and defining a central axis, the central axis being obliquely oriented relative to the longitudinal axis, the second opening extending through the rigid end effector and being coplanar with the first opening; and
a sensor disposed at a position along the longitudinal axis of the shaft assembly, the sensor being configured to provide a signal in response to a magnetic field, the signal configured to indicate a position of the rigid end effector within three-dimensional space.

13. The apparatus of claim 12, further comprising an insulating cuff captured between the sensor and the distal end of the shaft assembly.

14. A method, comprising:
inserting a rigid end effector of an instrument into a patient,
wherein the instrument comprises a shaft assembly extending along a longitudinal axis and fixed relative to the rigid end effector,
wherein the rigid end effector comprises a first opening that, is positioned along the longitudinal axis, is coplanar with a second opening that extends through the rigid end effector, and defines a central axis that is obliquely oriented relative to the longitudinal axis;
receiving signals from a sensor, the signals being provided in response to a magnetic field;
processing the signals received from the sensor using a processor, the processed signals indicating a real-time position of the rigid end effector;
displaying, in real-time on a display, the position of the rigid end effector within three-dimensional space based on the processed signals; and
engaging the rigid end effector with tissue in the patient based on the position.

15. The method of claim 14, wherein the rigid end effector comprises a loop blade.

16. The method of claim 14, wherein engaging the rigid end effector further comprises engaging a transversely extending portion of the rigid end effector with tissue in the patient based on the position.

17. The method of claim 14, further comprising communicating a fluid to a target site in the patient via the opening, which is positioned at a distal end of the instrument.

18. The method of claim 14, further comprising suctioning fluid away from a target site in the patient via the opening, which is positioned at a distal end of the instrument.

19. The apparatus of claim 1, wherein the opening has a diameter that is smaller than a second diameter of a second opening in the rigid end effector.

* * * * *